United States Patent [19]

Neisz

[11] Patent Number: 5,411,539
[45] Date of Patent: May 2, 1995

[54] ACTIVE CAN EMULATOR AND METHOD OF USE

[75] Inventor: Hans J. Neisz, Coon Rapids, Minn.

[73] Assignee: Medtronic, Inc., Minneapolis, Minn.

[21] Appl. No.: 114,719

[22] Filed: Aug. 31, 1993

[51] Int. Cl.$^6$ .......................................... A61N 1/375
[52] U.S. Cl. ..................................... 607/36; 607/27; 607/33; 607/116
[58] Field of Search ...................... 607/27, 29, 31, 33, 607/36, 37, 116, 119, 148

[56] References Cited

U.S. PATENT DOCUMENTS

| | | |
|---|---|---|
| 4,922,927 | 5/1990 | Fine et al. |
| 4,953,551 | 9/1990 | Mehra . |
| 5,105,809 | 4/1992 | Bach, Jr. et al. ................. 607/5 |
| 5,133,353 | 7/1992 | Hauser . |
| 5,324,312 | 6/1994 | Stokes et al. .................... 607/37 |

Primary Examiner—Lee S. Cohen
Assistant Examiner—Jeffrey R. Jastrzab
Attorney, Agent, or Firm—Reed A. Duthler; Harold R. Patton

[57] ABSTRACT

An active can emulator for emulating the electrical and dimensional characteristics of an implantable pulse generator of the type having a hermetically sealed housing configured to operate as an active electrode and a connector block for receiving and connecting with a lead extending to a second active electrode. The emulator comprises a reusable, sterilizable, conductive can conforming to the dimensional characteristics of the hermetically sealed housing of the implantable pulse generator and having a first electrical and mechanical connector and a disposable lead having a second electrical and mechanical connector for mating attachment with the first connector formed as part of a header configured to conform to the dimensional characteristics of the connector block of the emulated pulse generator. In use, the testing of defibrillation thresholds and system performance is conducted by implanting a transvenous lead bearing an electrode disposed in the patient's heart, creating the surgical pocket opening to receive the pulse generator, using the active can emulator to enlarge the surgical pocket while positioning it therein, coupling the transvenous lead and the lead of the active can emulator to an external cardioverter, inducing a tachyarrythmia in the patient's heart, and operating the external cardioverter to deliver one or more cardioverting pulses to the patient's heart through the two electrodes to determine whether or not the patient's heart can be satisfactorily cardioverted. The testing may be repeated with variations in the positioning of the active can emulator to locate a position providing a satisfactory safety factor. After testing is completed, the lead may be disposed of, but the can may be cleaned and resterilized conventionally and reused on other patients.

13 Claims, 3 Drawing Sheets

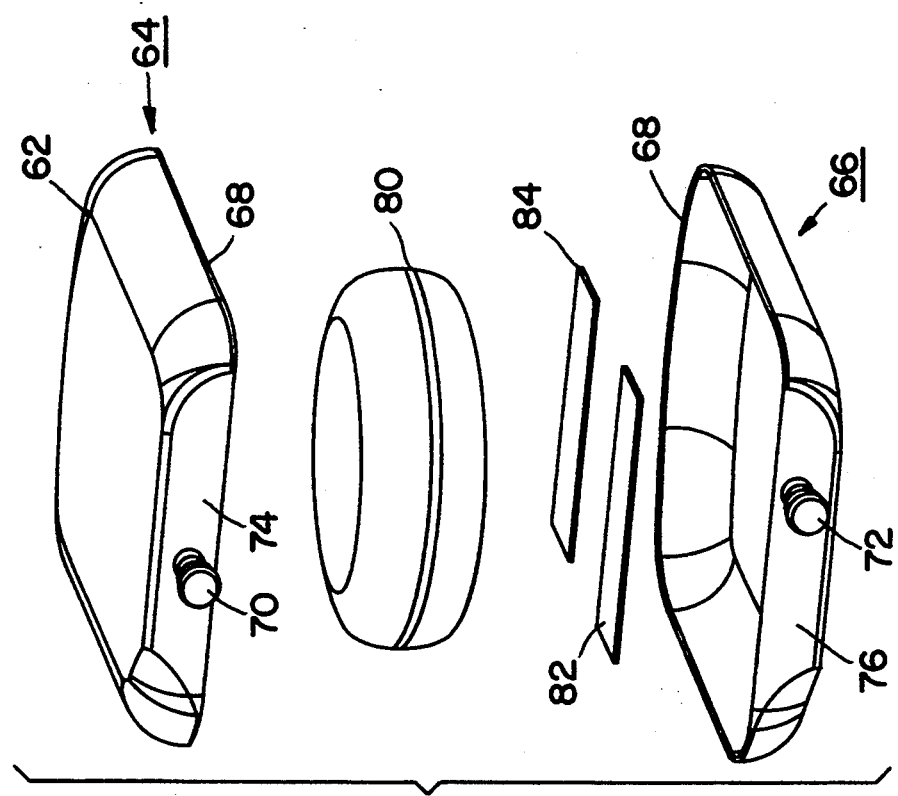
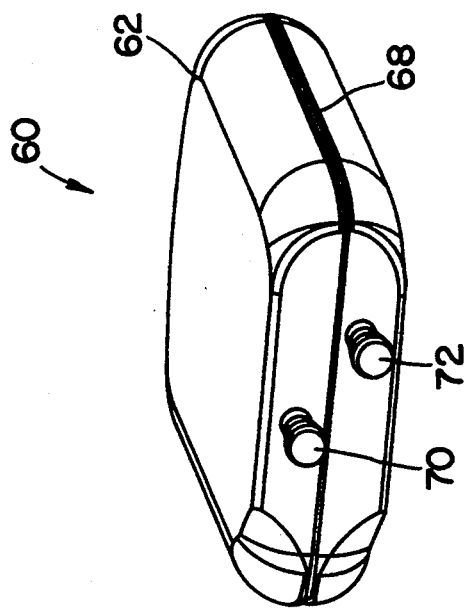

ACTIVE CAN EMULATOR AND METHOD OF USE

CROSS-REFERENCE TO RELATED APPLICATIONS

Reference is hereby made to commonly assigned, co-pending U.S. patent application Ser. No. 07/834,446, filed Feb. 12, 1992, in the name of Gust Bardy, M.D.

BACKGROUND OF THE INVENTION

1. Field of the Invention

The present invention relates to medical electrical leads generally, and more particularly to the emulation of defibrillation electrodes in the surgical work up of a patient for the implantation of a pulse generator having an active case electrode.

DESCRIPTION OF THE BACKGROUND ART

By way of definition, in the field of automatic implantable arrhythmia control devices, the term "cardioversion" or "cardioverter" refers to the process of and device for discharging relatively high energy electrical pulses into or across cardiac tissue to arrest a life threatening tachyarrhythmia. Cardioversion pulses may or may not be synchronized with a cardiac depolarization or rhythm and may be applied to arrest a ventricular tachycardia with a lower range energy pulse of around 1–15 joules or ventricular fibrillation with a medium to high energy pulse of 7–40 joules, nominally. The arrest of ventricular fibrillation by such pulses is referred to as "defibrillation", a form of cardioversion, and "defibrillators" have been characterized as a form of cardioverter. In the following description and claims, it is to be assumed that these terms are interchangeable, and that use of one term is inclusive of the other device or operation, unless specific distinctions are drawn between them in the context of the use.

Efforts to enhance efficacy and decrease cardioversion/defibrillation efficiency have led to the suggestion of lead systems employing endocardial electrodes and a subcutaneous electrode taking the form of some or all of the housing of the implantable cardioverter. U.S. Pat. No. 4,922,927, issued to Fine et al., proposes the use of an electrode system using a right ventricular lead and a subcutaneous electrode, which may correspond to prior art subcutaneous electrodes or may be the metal enclosure of the defibrillator. The right ventricular lead carries an elongated coil electrode. The Bardy '446 application first referenced above also discloses an implantable defibrillator having a conductive housing used as an electrode. In U.S. Pat. No. 5,133,353, issued to Hauser, a "mesh" electrode formed on a portion of the pulse generator case or housing is proposed to be employed as one electrode in a two or three electrode system.

As described briefly in the Bardy '446 application, acute human clinical testing has been conducted using a right ventricular defibrillation lead, carrying a single, platinum coil defibrillation electrode, and one half of a titanium housing of a Medtronic Model 7217 implantable defibrillator to gather threshold data on the potential efficacy of an active can electrode system. The "can" half has a total exposed surface area of approximately 100 square centimeters with the planar, major surface having an area of approximately 70 square centimeters. The can half was located in the left infraclavicular pectoral region and was employed as the cathode electrode during the initial phase of a biphasic defibrillation pulse. In such a configuration, it was determined that effective defibrillation at pulse energies of approximately eight joules could be achieved.

As a result of these improvements and findings in relation to the use of the pulse generator case as a subcutaneous electrode in certain implantation locations and with certain wave forms, implantable systems capable of being implanted and used in this fashion are being developed. A need exists for a simplified and inexpensive system for conducting the clinical tests for screening patients for the implantation of these systems when they become available for general clinical use.

SUMMARY OF THE INVENTION

Accordingly, it is an object of the invention to provide a simple and largely re-usable active can electrode emulator and method of use thereof for screening patients for suitability of permanent implantation with an electrode system employing an active can electrode.

It is a further object of the invention to form such an active can emulator having a major re-usable component and a minor disposable component.

It is a still further object of the present invention to provide a simplified method for conducting cardioversion efficacy patient testing with an emulation of an implantable defibrillator without surgically implanting all of the components of the actual implantable system.

The present invention is thus directed toward the method of testing a patient for suitability of implantation of a defibrillator pulse generator having an active housing surface electrode on its housing for use with at least a first lead bearing a remote electrode, wherein the testing is conducted by: implanting the first lead with the remote electrode in an intended position for permanent implantation; implanting a reusable, dummy housing shaped electrode, with a detachable and disposable connector and second lead attached thereto, the dummy housing shaped electrode having dimensional characteristics corresponding to those of the defibrillator pulse generator housing, in an expected position for permanent implantation of the pulse generator housing; coupling the first and second lead to an external cardioverter; inducing a tachyarrythmia in the patient's heart; operating the external cardioverter to deliver one or more cardioverting pulses to the patient's heart through the dummy housing electrode and the remote electrode to determine the pulse characteristics sufficient to effect cardioversion; removing the dummy housing electrode and second lead; detaching and disposing of the second lead and connector; and retaining the dummy housing for sterilization and reuse.

The method preferably is repeated with respect to the steps of: implanting the dummy housing and lead at further intended implantation locations of the pulse generator housing; inducing a tachyarrhythmia of the patient's heart at each such location; and delivering cardioversion pulses and determining the threshold energy necessary for successful cardioversion at each such position; and wherein the steps of removing, detaching and retaining are conducted after a suitable position is found for permanent implantation of the implantable defibrillator pulse generator.

In a second aspect of the invention, an active can emulator for emulating the electrical and dimensional characteristics of an implantable pulse generator of the type having a hermetically sealed housing configured to operate as an active electrode and a connector block for receiving and connecting with a lead comprises: a reusable, sterilizable, conductive can conforming to the dimensional characteristics of the hermetically sealed housing and having a first electrical and mechanical attachment mechanism; and a disposable lead having a second electrical and mechanical attachment mechanism for mating attachment with said first electrical and mechanical attachment mechanism and means configured to conform to the dimensional characteristics of said connector block upon attachment of said first and second electrical and mechanical attachment mechanisms.

In respect to this aspect of the invention, an active can emulator for testing the locations of implantation of an electrical pulse generator enclosed in a housing having predetermined electrode dimensions and connector dimensions comprises: an emulator housing having an electrode shaped to conform to the electrode dimensions of said housing of the implantable pulse generator; a first connector element attached to said emulator housing for electrical connection therewith; and a detachable lead having a second connector element adapted to make electrical and mechanical contact with said first connector element, said second connector element of said detachable lead shaped to conform to said connector dimensions of said connector of said pulse generator housing.

The active can emulator including the reusable can and disposable lead is preferably fabricated with dimensions, weight, balance and "feel" with the lead attached, and with the same active surface electrode size and shape, that corresponds to the actual defibrillator pulse generator intended to be implanted in the patient.

In a preferred embodiment of the invention, the active can emulator is employed in testing of patients which are receiving an endocardial lead bearing an active electrode located in the right ventricle and a second active electrode formed on the housing or can of a defibrillator pulse generator that is adapted to be coupled to the endocardial lead through a connector block. The defibrillator pulse generator is subcutaneously located in the left, pectoral region of the chest, rather than at the level of the ventricles. The pulse generator preferably delivers a monophasic or a symmetrical or asymmetrical, biphasic capacitive discharge pulse between the two electrodes, e.g., of the type illustrated in U.S. Pat. No. 4,953,551, issued to Mehra et al., wherein the initial phase of the pulse is delivered using the subcutaneous electrode as the cathode (coupled to the negatively charged terminal of the output capacitor during the initial phase).

The active can emulator of the present invention has the important advantages of simplicity of construction and of use in the pre-implantation screening of patient's ability to benefit from the above described cardioversion system. The active can emulator is advantageously fabricated so that the can is reusable through standard autoclave or ethylene oxide sterilization, and only the more porous lead and connector need be disposed of.

BRIEF DESCRIPTION OF THE DRAWINGS

These and other advantages, objects and features of the invention will be further understood when reference is made to the following description, taken in conjunction with the accompanying drawings, in which:

FIG. 2 is a perspective view of the dummy can employed as the reusable portion of the active can emulator according to an embodiment of the present invention;

FIG. 3 is an exploded perspective view of the components of the dummy can of FIG. 2;

The drawings are not necessarily to scale.

DETAILED DESCRIPTION OF THE PREFERRED EMBODIMENT

Figure 1:
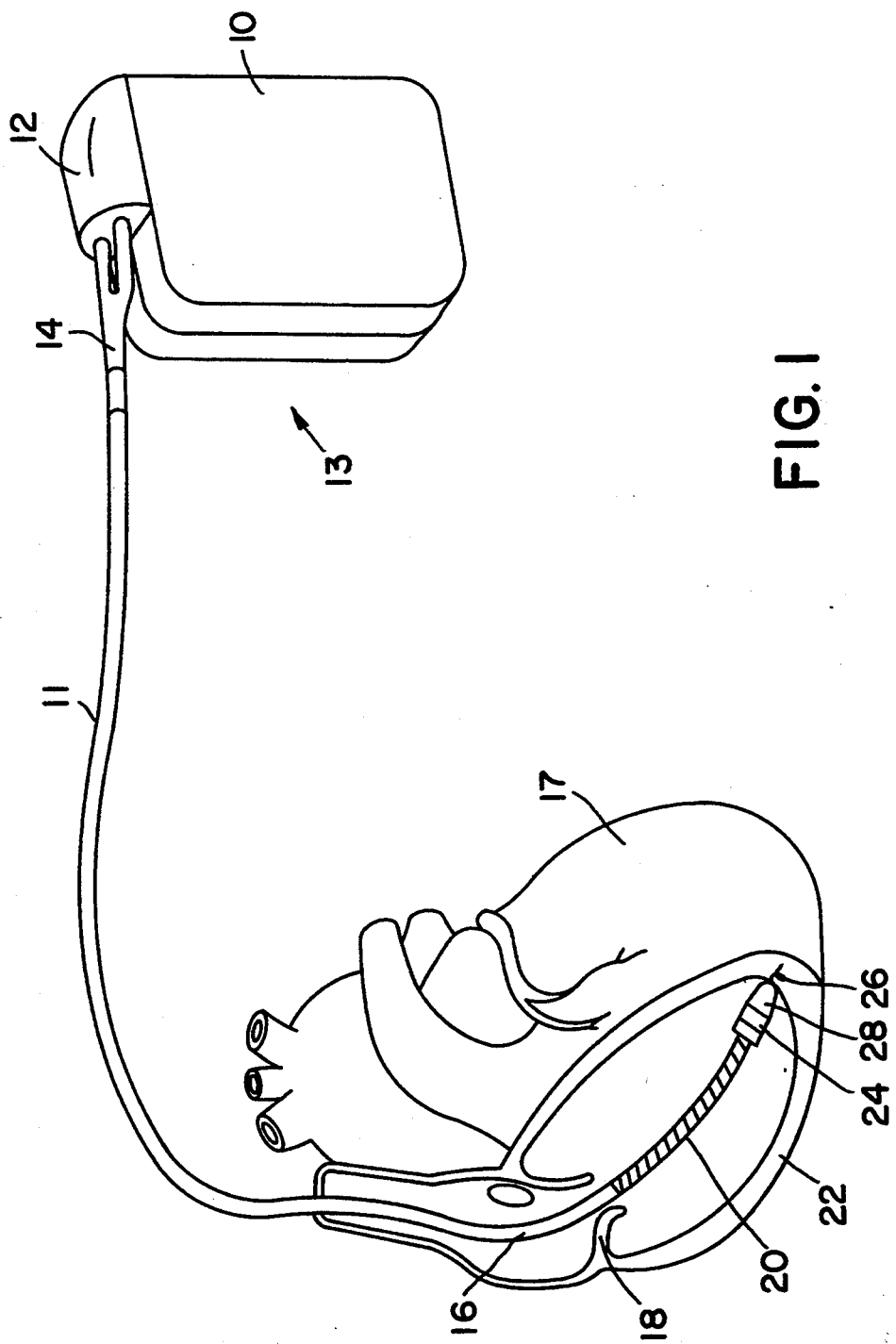
FIG. 1 illustrates the implantable defibrillator and lead system in which the invention may be employed prior to implantation of the system.

FIG. 1 illustrates a combined defibrillator pulse generator housing and active electrode 10, which would be implanted, according to the present invention, in conjunction with a transvenous lead 11 extending into the right ventricle of a heart 17. Lead 11 is exemplary of the type of lead that may be employed in conjunction with the present invention, but any of the various transvenous defibrillation leads presently on sale or in clinical evaluation may be employed as well. The lead 11 includes an elongated insulated lead body 16, carrying three concentric coiled conductors, separated from one another by tubular insulative sheaths. Located adjacent the distal end of the lead 11 are a ring electrode 24, an extendable helix electrode 26, mounted for retractable movement within an insulative electrode head 28, and an elongated coil electrode 20. The defibrillation electrode 20 may be fabricated from platinum, platinum alloy or other materials known to be usable in implantable defibrillation electrodes. Electrodes 24 and 26 are employed for cardiac pacing and for sensing ventricular depolarizations.

Each of the electrodes 20, 24 and 26 is coupled to one of the coiled wire conductors within the lead body 16. At the proximal end of the lead is a bifurcated connector 14 which carries three electrical connectors (not shown), each coupled to one of the coiled wire conductors. The two connectors coupled by coiled wire conductors to the pace/sense electrode pair 24, 26 are arranged on a common connecter pin, and the other connector coupled by a further coiled wire conductor to the defibriilation electrode 20 forms the second connector pin of the bifurcated connector 14.

The implantable defibrillator housing 10 comprises an active electrode formed by attaching it to a defibrillation circuit output terminal. The housing or can 10 may have engraved information on one major exposed surface that is intended to be implanted facing outward. The defibrillator housing 10 is formed with a connector block 12, into which the bifurcated connector 14 is inserted and mechanically attached. The housing 10 and connector block 12 is typically referred to as a defibrillator pulse generator and is referenced collectively as 13.

In the preferred embodiment, the pulse generator 13 is a multi-programmable device that provides bradycardia and anti-tachycardia pacing, cardioversion and defibrillation, depending on the nature of the detected heart rhythm and programmed-in operating modes. A specific example of a pacing/cardioversion/defibrillation pulse generator 13, which may be used in conjunction with the illustrated lead system to deliver biphasic pulses, is disclosed in U.S. Pat. No. 4,953,551, issued to Mehra et al., incorporated herein by reference in its entirety. The size and shape of the pulse generator 13 may differ from that illustrated in FIG. 1.

The connector block 12 of the pulse generator 13 is molded of a biocompatible, electrically insulating epoxy compound that has been employed for many years in the fabrication of such devices to support and insulate the connector components from one another and from body fluids. Such epoxy compounds are, however, difficult to sterilize once they are exposed to blood and body fluids. Consequently, re-use of a functioning pulse generator 13 on another patient is not advised even if the pulse generator is exposed only briefly in the attempt to implant it in a patient. Inasmuch as implantable defibrillators of the type specified are rather expensive, it is undesirable to expose them to the patient during the pre-implantation work-up that includes testing the defibrillation thresholds of the electrode and pulse generator system at one or more implantation systems.

Similarly, implantable leads are typically constructed to high standards and with relatively expensive components. The insulation employed in such leads is also contaminated by blood and body fluids, and such leads are not recommended for sterilization and reuse. Temporary leads used in acute patient care or testing are constructed of less expensive materials and are typically disposed of after use on a single patient.

Pre-implantation threshold testing is conducted to obtain a reasonable assurance that the pulse energy available exceeds the threshold necessary to cardiovert the patient's heart (in which fibrillation or a high rate tachycardia is induced) by an acceptable safety margin. The tests may be conducted using an external device having all the capabilities of the implanted defibrillator that is connected to the electrodes expected to be used in the implanted system. All of the functions of the implanted system may thus be emulated without exposing the implanted pulse generator.

In addition, use of the implanted device in the testing procedure is awkward and may pose dangers to operating room staff as fibrillation episodes are induced and responded to by the device. It may be difficult to determine just when a shock will be delivered by the device in response to an induced tachyarrhythmia, risking a shock being delivered while the device is being handled.

As described above, can halves have been used for experimental testing of the concept of using an active can electrode as one of the electrodes of the electrode system. However, the can halves have been awkward to use and to attach leads to. Consequently, the use of such can halves for clinical use in conducting the pre-implant threshold tests is not considered acceptable. "Dummy" cans mimicking the size and shape of the implanted pulse generator 13 having suitable connector blocks attached thereto for connection by a temporary lead to the external cardioverter/defibrillator would not be reusable in conducting such tests in other patients. Moreover, they would add further acquisition and disposal costs to the procedure for each patient.

Figure 4:
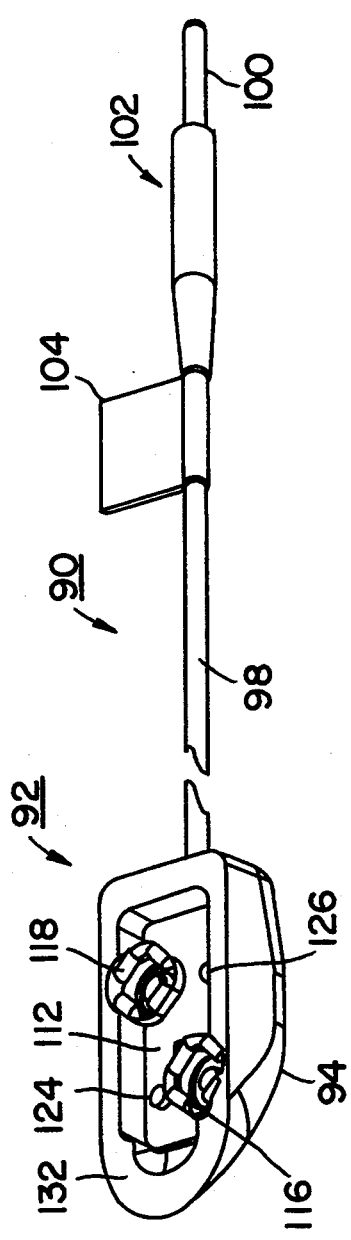
FIG. 4 is a perspective view of the disposable lead and connector block adapted to be attached to the dummy can of FIGS. 2 and 3.
Figure 6:
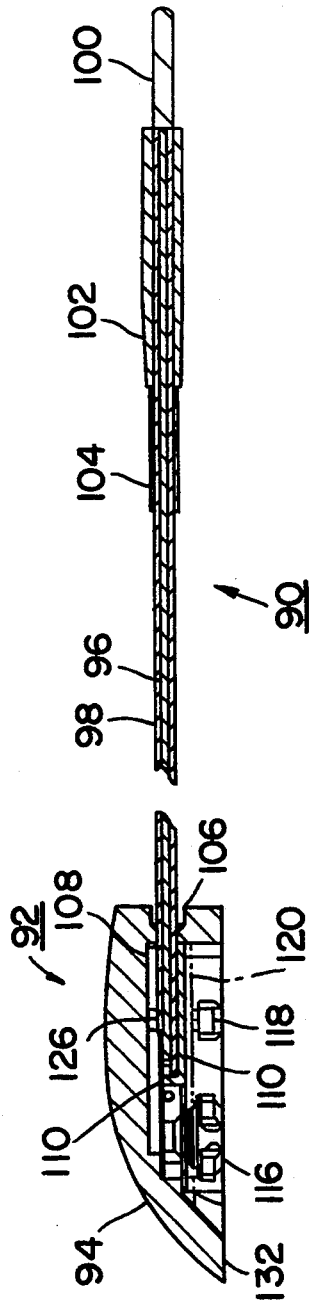
FIG. 6 is a side sectional view of the disposable lead and connector block adapted to be attached to the dummy can of FIGS. 2 and 3.
Figure 5:
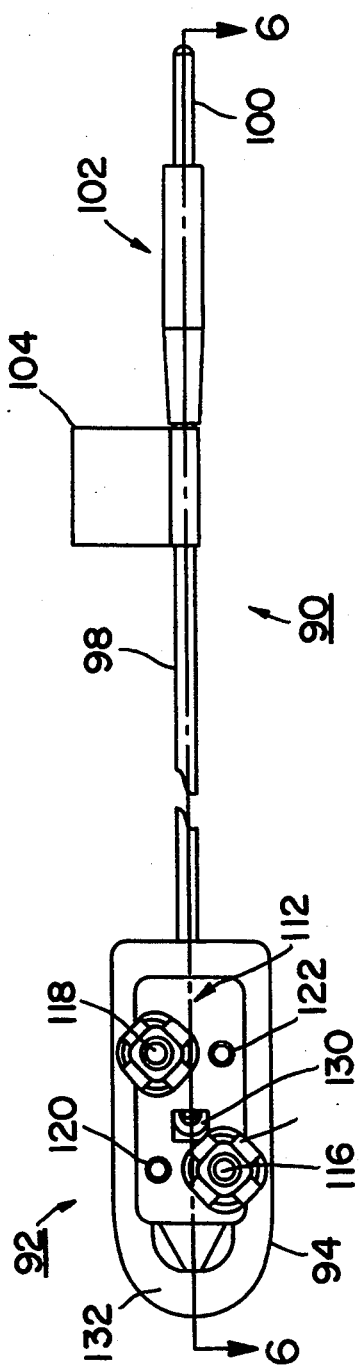
FIG. 5 is a bottom view of the disposable lead and connector block adapted to be attached to the dummy can of FIGS. 2 and 3.

Turning to FIGS. 2 and 3, one embodiment of the reusable can component 60 of the active can emulator 50 is depicted in greater detail in perspective and exploded views. In FIGS. 4-6, one embodiment of the disposable component 90 of the active can emulator 50 is depicted in several views. The active can emulator 50 is completed by the attachment together of the components 60 and 90 in a manner to be described. When so attached, the combination of the can component 60 and the distal end 92, specifically the connector block emulator header 94, is of a size, weight and shape that it emulates the pulse generator housing 10 and connector block 12 of the implantable defibrillator depicted in FIG. 1.

In particular, the un-insulated and electrically active surface electrode 62 is shaped to conform to that of the pulse generator housing 10, so that a cardioversion pulse may be applied through the surface electrode 62 in the same fashion that it would if the implantable defibrillator were itself implanted in the same location. The entire exterior metallic surface of the can component 60 is expected to be exposed, so that it matches the fully exposed electrode configuration of the actual defibrillator pulse generator housing 10.

Turning to the can component 60 depicted in FIGS. 2 and 3, it is formed by enclosing parts described below, welding two mirror image can halves 64 and 66 together at welding seam 68, testing the integrity of the weld seam, and polishing and engraving the outer surface to a finish mimicking the emulated pulse generator housing leaving the active electrode 62 exposed. Each can half has a male connector element 70 or 72 protruding from a respective end 74 or 76. The male connector elements 70 and 72 are electrically and mechanically attached to the can halves 64 and 66, respectively, by welding or the like, so that a secure and redundant electrical and mechanical attachment may be made to the mating connector elements in the connector block emulator portion 94 described hereafter. The male connector elements 70 and 72 may be simple nine volt battery, snap connector male connector elements that snap into and out of mating female connector elements.

In order to emulate the weight and balance of the actual pulse generator housing, a weight 80 formed of aluminum is placed within the can halves 64 and 66.

The weight 80 may be dimensioned so that it is tightly contacted when the can halves 64 and 66 are welded together. A pair of double sided tape strips 82 and 84 can be adhered to the interior surface of can half 66 and to one surface of the weight 80 to also stabilize the weight 80 prior to seam welding the can halves 64 and 66. Further strips of tape may be employed between the interior surface of the can half 64 and the other surface of the weight 80. Silicone adhesive may also be employed to reinforce the attachment.

Other weight shapes and attachment mechanisms may be substituted for that shown and described above. The effect sought is the emulation of the weight, balance and feel of the actual pulse generator housing without having the internal weight move around and change the balance. In testing the fit of the surgical pocket made to accommodate the defibrillator pulse generator, the surgeon considers whether the implanted device will be retained in place or have a tendency to migrate and change the electrode pathways, which could render the system ineffectual.

The can component 60 thus forms one part of the active can emulator 50 which is completed on attachment of the lead component 90 and particularly the connector block emulating header 94 thereto. The lead component 92 is constructed of a single wire conductor 96 insulated by a tubular sheath 98 extending between the header 94 at the distal end 92 and to a connector pin 100 at the proximal connector end 102. An identification tag 104 is attached to the sheath 98 which bears an identification and instruction "NOT FOR RE-USE".

The header 94 is formed of a compound of the type used to form the connector block of the emulated defibrillator pulse generator and is sized and shaped to mimic it. The distal end of the conductor extends through an end opening 106 and into the interior space 108 as shown in FIG. 6 and into abutment with a tab 110 of a conductive plate 112 which fits into the interior space or recess 108. The conductive plate 112 has a pair of female nine volt battery snap connector elements attached to it and spaced to receive the male connector elements 70 and 72. The plate 112 is positioned within recess 108 by its peripheral shape and a pair of holes 120 and 122 which receive positioning pins 124 and 126 formed as part of the header 94. Attachment of the distal end of the conductor 96 is effected by a spot weld or solder joint of the conductor to the tab 110 effected through opening 130. Conductive adhesives may also be used in the opening 130, and the entire assembly may be secured with adhesives applied at contacting edges of the components, as long as the adhesive does not interfere with attachment of the male and female connector elements.

When the components 60 and 90 are attached, the edge 132 of the header 94 bears against the flat end surfaces 74 and 76 of the can halves so that the active can emulator 50 mimics the weight balance, feel and overall dimensions of the implantable defibrillator pulse generator.

In such use, the testing of defibrillation thresholds and system performance is conducted by implanting a first lead having a remote electrode (that is the transvenous right ventricular electrode in the preferred two electrode system shown in FIG. 1) in the intended position for permanent implantation, creating the surgical pocket to receive the pulse generator and implanting the active can electrode emulator in the surgical pocket, coupling the first lead and the lead of the active can emulator to an external cardioverter/defibrillator, inducing a tachyarrythmia in the patient's heart, and operating the external cardioverter to deliver one or more cardioverting pulses to the patient's heart through the active can electrode emulator and the remote electrode to determine whether or not the patient's heart can be cardioverted at a satisfactory threshold. The testing may be repeated with variations in the positioning of the active can emulator to locate a position providing a satisfactory safety factor. After testing is completed, the lead component 90 may be disposed of, but the can component 60 may be cleaned and re-sterilized by conventional autoclaving or gas sterilization and reused.

The active can electrode emulator components 60 and 90 are also useful in preparing the surgical pocket in which the permanent implantable pulse generator may be positioned. In the course of conducting the threshold tests, a surgical pocket may be made subcutaneously in a pectoral or abdominal position relative to the heart and the indwelling electrode using the component 60 in enlarging the opening and insuring that it is properly sized. This avoids using the pulse generator itself, which could be damaged in such handling, and avoids contamination if for any reason it is later found that the placement achieved is not sufficient.

Although a variety of embodiments of the invention have been depicted and described, it will be understood that further variations and alternatives will suggest themselves to those of skill in the art. For example, although the construction of the active can emulator described above is preferred, it will be understood that other construction and fabrication techniques and materials may be employed to emulate the size, shape, weight and materials employed in the fabrication of the mimicked pulse generator.

Although it is contemplated that the active can electrode emulator of the invention will mimic pulse generator cases which will have the capability of being used as active can electrodes and will have polished exterior surfaces with engraving on one major surface, the invention may be employed in emulators mimicking pulse generators having mesh electrodes of the type referred to above or other electrodes attached thereto. Moreover, while it is anticipated that the entire case or can surface of the pulse generator is expected to be exposed to act as an electrode, it will be understood that the emulators and their methods of use of the present invention will be applicable to pulse generators having partially insulated surfaces. In such a situation, a further removable and replaceable "boot" may be supplied to fit over the insulated areas of the case or can of the pulse generator being mimicked. The replaceable boot of silicon rubber or the like may be removed and discarded after use and prior to cleaning and sterilization of the emulator component 60.

Accordingly, it will be understood that various changes and modifications may be made without departing from the broader aspects of this invention. It is therefore the intention in the appended claims to cover all such changes and modifications as fall within the true spirit and scope of this invention.

In conjunction with the above specification, I claim:

1. A pulse generator emulator operable as a subcutaneous electrode for use with at least one remote electrode in testing the efficacy of electrical stimulation of a body organ with an implantable pulse generator, comprising:

an emulator housing, configured to emulate the characteristics of a hermetically sealed housing of an implantable pulse generator of the type having a connector block attached thereto, said emulator housing having an electrode on a surface thereof and first connector means attached to the emulator housing for making electrical connection to the electrode; and an elongated lead including a conductor extending from a proximal end to a distal end thereof, a second connector means for coupling to a defibrillator, located at the proximal end and coupled to said conductor, a header permanently mounted to the distal end of the lead configured to emulate the connector block of the implantable pulse generator and third connector means mounted to said header and coupled to said conductor, for removably connecting with said first connector means.

2. The emulator of claim 1 wherein said first connector means and said third connector means further each comprise a pair of spaced apart connector elements for providing redundant electrical connection of the proximal end of the lead to the electrode on the emulator housing and for inhibiting relative movement of the header with respect to the emulator housing when mechanical attachment is made.

3. The emulator of claim 2 wherein said first connector means comprises a pair of spaced-apart male connector elements extending from said emulator housing for providing redundant electrical connection to said emulator housing and said third connector means comprises a pair of female connector elements spaced-apart in the same manner as said pair of male connector elements and electrically connected to one another for providing redundant electrical connection between said proximal end of said lead and said electrode on said emulator housing and for inhibiting relative movement of said header with respect to said emulator housing when mechanical attachment is made.

4. The emulator of claim 2 wherein said lead is adapted to be disposed of after use in emulation of a stimulation regimen in a single patient and said emulator housing is constructed of sterilizable materials and adapted to be sterilized and reused after use in a single patient.

5. The emulator of claim 1 wherein said lead is adapted to be disposed of after use in emulation of a stimulation regimen in a single patient and said emulator housing is constructed of sterilizable materials and adapted to be sterilized and reused after use in each patient.

6. A method of testing a patient for suitability of implantation of a defibrillator pulse generator having a housing and an active housing surface electrode on its housing for use with at least a first lead bearing a remote electrode, wherein the testing is conducted by:
   implanting the first lead with the remote electrode in an intended position for permanent implantation;
   implanting a reusable, dummy housing shaped electrode, with a detachable and disposable connector and second lead attached thereto, the dummy housing shaped electrode having dimensional characteristics corresponding to those of the defibrillator pulse generator housing, in an expected position for permanent implantation of the pulse generator housing;
   coupling the first and second lead to an external cardioverter;
   inducing a tachyrhythmia in the patient's heart; and operating the external cardioverter to deliver one or more cardioverting pulses to the patient's heart through the dummy housing shaped electrode and the remote electrode to determine pulse characteristics sufficient to effect cardioversion.

7. The method of claim 6 further comprising the steps of:
   removing the dummy housing shaped electrode and second lead from the implant site;
   detaching and disposing of the second lead and connector; and
   retaining the dummy housing shaped electrode for cleaning, sterilization and reuse.

8. The method of claim 7 further comprising repeating the steps of:
   implanting the dummy housing shaped electrode and second lead at further intended implantation locations of the pulse generator housing;
   inducing a tachyarrhythmia of the patient's heart at each such location; and
   delivering cardioversion pulses and determining a threshold energy necessary for successful cardioversion at each such position.

9. The method of claim 8 further comprising the step of identifying a suitable position for permanent implantation of the implantable pulse generator and wherein the steps of removing, detaching and retaining are conducted after a suitable position is identified.

10. The method of claim 6 wherein:
   the step of implanting the first lead further comprises:
   transvenously implanting the first lead with the remote electrode in contact with the patient's heart;
   and the step of implanting a reusable, dummy housing shaped electrode, with a detachable and disposable connector and second lead attached thereto comprises:
   surgically creating a subcutaneous pocket beneath the patient's skin; and
   inserting the dummy housing shaped electrode into the subcutaneous pocket, facing toward the patient's heart, with the second lead extending from the subcutaneous pocket for attachment to the external cardioverter.

11. The method of claim 6 wherein the step of operating the external cardioverter further comprises the step of:
   delivering an asymmetrical, biphasic capacitive discharge pulse between the remote electrode and the dummy housing shaped electrode.

12. A method of testing defibrillation thresholds and system performance of an implantable defibrillator pulse generator and electrode system of the type having a hermetically sealed housing surface configured to operate as a first active electrode and a connector block for receiving and connecting with an implantable lead comprising a second active electrode comprising the steps of:
   providing an active can emulator for emulating the electrical and dimensional characteristics of the implantable pulse generator and comprising a reusable, sterilizable, conductive can conforming to the dimensional characteristics of the hermetically sealed housing surface of the implantable pulse generator and having a first electrical and mechanical connector and a disposable lead having a second electrical and mechanical connector for mating attachment with the first connector formed as part of a header configured to conform to the dimensional characteristics of the connector block of the implantable pulse generator;
   implanting the implantable lead with the remote electrode disposed in relation to a patient's heart;
   creating a surgical pocket to receive the implantable pulse generator;
   implanting the active can emulator in the surgical pocket;
   inducing a tachyrhythmia in the patient's heart; and
   delivering one or more cardioverting pulses to the patient's heart through the first and second active electrodes to determine whether or not the patient's heart can be satisfactorily cardioverted.

13. The method of claim 12 further comprising the steps of:
   removing the active can emulator from the surgical pocket after testing is completed;
   disconnecting and disposing of the disposable lead; and
   cleaning, resterilizing and retaining the conductive can for reuse in testing other patients.

* * * * *